(12) United States Patent
Shrestha et al.

(10) Patent No.: US 8,976,763 B2
(45) Date of Patent: Mar. 10, 2015

(54) METHOD AND SYSTEM FOR ALLOCATION GUARANTEED TIME SLOTS FOR EFFICIENT TRANSMISSION OF TIME-CRITICAL DATA IN IEEE 802.15.4 WIRELESS PERSONAL AREA NETWORKS

(75) Inventors: Bharat Shrestha, Winnipeg (CA); Abu Zafar Ekram Hossain, Winnipeg (CA); Sergio Guido Camorlinga, Winnipeg (CA); Rajagopalan Krishnamoorthy, Winnipeg (CA); Dusit Niyato, Singapore (SG)

(73) Assignee: Telecommunications Research Laboratories, Edmonton, ALberta (CA)

( * ) Notice: Subject to any disclaimer, the term of this patent is extended or adjusted under 35 U.S.C. 154(b) by 500 days.

(21) Appl. No.: 12/974,718

(22) Filed: Dec. 21, 2010

(65) Prior Publication Data

US 2011/0158206 A1    Jun. 30, 2011

Related U.S. Application Data (60) Provisional application No. 61/288,703, filed on Dec. 21, 2009.

(51) Int. Cl.
*H04W 72/10*    (2009.01)
*H04W 72/12*    (2009.01)
(Continued)

(52) U.S. Cl.
CPC ........... *H04W 72/1252* (2013.01); *G01D 21/00* (2013.01); *A61B 5/0024* (2013.01); *A61B 5/02055* (2013.01); *A61B 5/021* (2013.01); *A61B 5/0402* (2013.01); *A61B 5/08* (2013.01); *A61B 5/11* (2013.01); *A61B 5/14532* (2013.01); *A61B 5/14551* (2013.01); *A61B 2562/0219* (2013.01); *G06F 19/3418* (2013.01); *H04W 72/0413* (2013.01); *H04W 72/042* (2013.01);
(Continued)

(58) Field of Classification Search
USPC ......................................................... 370/336
See application file for complete search history.

(56) References Cited

U.S. PATENT DOCUMENTS 8,335,244 B2 * 12/2012 Liu ................................ 375/133
2006/0013133 A1 * 1/2006 Peng et al. .................... 370/230
(Continued)

FOREIGN PATENT DOCUMENTS

CN         101667849 A  *  3/2010
WO    WO 2010025680 A1 *  3/2010

OTHER PUBLICATIONS

Bharat Shrestha, et al., "An Optimization-Based GTS Allocation Scheme for IEEE 802.15.4 MAC with Application to Wireless Bod-Area Sensor Networks", in the Proceedings of IEEE International Conference on Communications (ICC 2010), 6 pages.
(Continued)

*Primary Examiner* — Mark Rinehart
*Assistant Examiner* — Ellen A Kirillova
(74) *Attorney, Agent, or Firm* — J. Jay Haugen; Dentons Canada LLP (57) ABSTRACT

A guaranteed time slot allocation scheme is provided for the IEEE 802.15.4 standard for use in wireless personal area networks having sensor devices to overcome bandwidth under-utilization for time-critical or delay-sensitive data transmissions. A fractional knapsack problem is formulated to obtain optimal guaranteed time slot allocation with which a minimum bandwidth requirement is guaranteed for the sensor devices.

11 Claims, 7 Drawing Sheets

(51) Int. Cl.

| | |
|---|---|
| *G01D 21/00* | (2006.01) |
| *A61B 5/00* | (2006.01) |
| *A61B 5/0205* | (2006.01) |
| *A61B 5/021* | (2006.01) |
| *A61B 5/0402* | (2006.01) |
| *A61B 5/08* | (2006.01) |
| *A61B 5/11* | (2006.01) |
| *A61B 5/145* | (2006.01) |
| *A61B 5/1455* | (2006.01) |
| *G06F 19/00* | (2011.01) |
| *H04W 72/04* | (2009.01) |
| *H04W 74/02* | (2009.01) |
| *H04W 74/04* | (2009.01) |
| *H04W 74/08* | (2009.01) |
| *H04W 84/10* | (2009.01) |
| *H04W 84/18* | (2009.01) |

(52) U.S. Cl.
CPC ....... *H04W72/0446* (2013.01); *H04W 72/1242* (2013.01); *H04W 74/02* (2013.01); *H04W 74/04* (2013.01); *H04W 74/08* (2013.01); *H04W 84/10* (2013.01); *H04W 84/18* (2013.01)
USPC ........................................................ 370/336

(56) References Cited

U.S. PATENT DOCUMENTS

| | | | | |
|---|---|---|---|---|
| 2008/0253372 | A1* | 10/2008 | Chan et al. | 370/392 |
| 2009/0318779 | A1* | 12/2009 | Tran | 600/301 |

OTHER PUBLICATIONS

M. A. Hanson, H. C. Powell Jr., A. T. Barth, K. Ringgenberg, B. H. Calhoun, J. H. Aylor, and J. Lach, "Body area sensor networks: Challenges and opportunities," IEEE Computer, vol. 42, No. 1, Jan. 2009.

IEEE Standard for Information Technology Part 15.1: Wireless medium access control (MAC) and physical layer (PHY) specifications for wireless personal area networks (WPANs), IEEE Standard 802.15.1 Working Group Std., 2005.

IEEE Standard for Information Technology Part 15.4: Wireless Medium Access Control (MAC) and Physical Layer (PHY) Specifications for Low-Rate Wireless Personal Area Networks (LR-WPANs), IEEE Standard 802.15.4 Working Group Std., 2006.

J. Espina, T. Falck and O. Mulhens, "Network topologies, communication protocols,and standards," Body Sensor Networks, Ed. G.Z. Yang, Springer, London, 2006.

J. Noga and V. Sarbua, "An online partially fractional knapsack problem," in Proceedings of the 8th International Symposium on Parallel Architectures, Algorithms and Networks (ISPAN'05), Dec. 2005.

P. Kumar, M. Gunes, A. Al Mamou, and I. Hussain, "Enhancing IEEE 802.15.4 for low-latency, bandwidth, and energy critical WSN applications," in Proceedings of 4th International Conference on Emerging Technologies (ICET'08).

Y.-K. Huang, A.-C. Pang, and H. N. Hung, "An adaptive GTS allocation scheme for IEEE 802.15.4," IEEE Transactions on Parallel and Distributed Systems, vol. 19, No. 5, May 2008.

A. Koubaa, M. Alves, and E. Tovar, "i-GAME: An implicit GTS allocation mechanism in IEEE 802.15.4 for time-sensitive wireless sensor networks," in Proceedings of the 18th Euromicro Conference on Real-Time Systems, 2006.

C. Na, Y. Yang, and A. Mishra, "An optimal GTS scheduling algorithm for time-sensitive transactions in IEEE 802.15.4.networks," Computer Networks, vol. 52, No. 13, pp. 2543-2557, Sep. 2008.

L. Cheng, A. G. Bourgeois, and X. Zhang, "A new GTS allocation scheme for IEEE 802.15.4 networks with improved bandwidth utilization," in Proceedings of International Symposium on Communications and Information Technologies (ISCIT'07), 2007.

U. Varshney, "Pervasive healthcare and wireless health monitoring," Mobile Networks and Applications, vol. 12, No. 2-3, Springer Netherlands, Jun. 2007.

T. Aoyagi, J. Takada, K. Takizawa, N. Katayama, T. Kobayashi, K. Y. Yazdandoost, H. B. Li, and R. Kohno, "Channel models for wearable and implantable WBANs," IEEE 802.15 Working Group Document, IEEE 802.15-08-0416-02-0006, Jul. 2008.

J. Takada, T. Aoyagi, K. Takizawa, N. Katayama, T. Kobayashi, K. Y. Yazdandoost, H. b. Li, and R. Kohno, "Static propagation and channel models in body area," COST 2100 6th Management Committee Meeting, TD(08)639, Lille, France, Oct. 2008.

A. Ahmad, A. Riedl, W. J. Naramore, N. Y. Chou, and M. S. Alley, "Scenario-based traffic modeling for data emanating from medical instruments in clinical environment," 2009 WRI World Congress on Computer Science and Information Engineering, Mar. 31-Apr. 2, 2009.

Y.-K. Huang, A.-C. Pang, and T.-W. Kuo, "AGA: Adaptive GTS allocation with low latency and fairness considerations for IEEE 802.15.4," IEEE International Conference on Communications (ICC), Istanbul, Turkey, 2006.

T. H. Cormen, C. E. Leiserson, R. L. Rivest, and C. Stein, Introduction to Algorithms, The MIT press, Cambridge, Massachusetts, 2001, in its entirety.

* cited by examiner

| bits: 0-3 | 4 | 5 | 6-7 |
|---|---|---|---|
| GTS Length | GTS Direction | Characteristics Type | Reserved |

METHOD AND SYSTEM FOR ALLOCATION GUARANTEED TIME SLOTS FOR EFFICIENT TRANSMISSION OF TIME-CRITICAL DATA IN IEEE 802.15.4 WIRELESS PERSONAL AREA NETWORKS

CROSS REFERENCE TO RELATED APPLICATIONS

This application claims priority of U.S. provisional patent application Ser. No. 61/288,703 filed Dec. 21, 2009, which is incorporated by reference herein in its entirety.

TECHNICAL FIELD

The present disclosure is related to the field of health care monitoring system using the Institute of Electrical and Electronics Engineers ("IEEE") 802.15.4 standard for wireless personal area networks, in particular, to methods for allocating guaranteed time slots for time critical and delay-sensitive data transmission in such networks and, in particular, wireless body area sensor networks.

BACKGROUND

Wireless body area sensor network ("WiBaSe-Net") [1] is an emerging technology that can be used in medical, entertainment, and fitness applications. In a WiBaSe-Net, several wearable or implanted sensor devices, for instance electrocardiogram ("ECG") sensor, blood pressure sensor, blood glucose sensor, temperature sensor, respiratory sensor, pulse oximeter, and accelerometer, are deployed throughout the body. A body controller unit ("BCU") collects data from the sensor devices and sends it to the medical center.

The IEEE 802.15.1 [2] and the IEEE 802.15.4 [3] based technologies will be suitable for WiBaSe-Nets [4]. IEEE 802.15.4 supports not only contention based access mechanism but also guaranteed time slot ("GTS") scheme under beacon-enabled mode for delay-sensitive applications.

GTS transmission can avoid packet drop due to collisions in the contention-based protocol (i.e., "CSMA/CA"), limited number of allowable retransmissions and number of backoffs as specified in the standard. In a medical sensor network, GTS allocation can also reduce the energy consumption of the sensor nodes due to carrier sensing. The IEEE 802.15.4 standard allocates GTS slots to devices in first-come first-serve ("FCFS") fashion. The IEEE 802.15.4 standard has been developed for use in wireless personal area networks ("WPAN"). This standard only supports a limited number of GTS for time-critical or delay-sensitive data transmission. Due to the lack of optimization, this standard allocation results in wastage of bandwidth while serving asymmetric traffic from different sensor devices.

IEEE 802.15.4[3] specifies the MAC protocol for low data rate short-range wireless networks such as medical wireless sensor networks. It can support two operating modes: beacon-enabled and non-beacon-enabled modes. In non-beacon-enabled mode, the unslotted carrier can sense multiple access with collision avoidance ("CSMA/CA") protocol is used. In beacon-enabled mode, the network coordinator can transmit a beacon to synchronize and provide necessary information to the devices.

Figure 1:
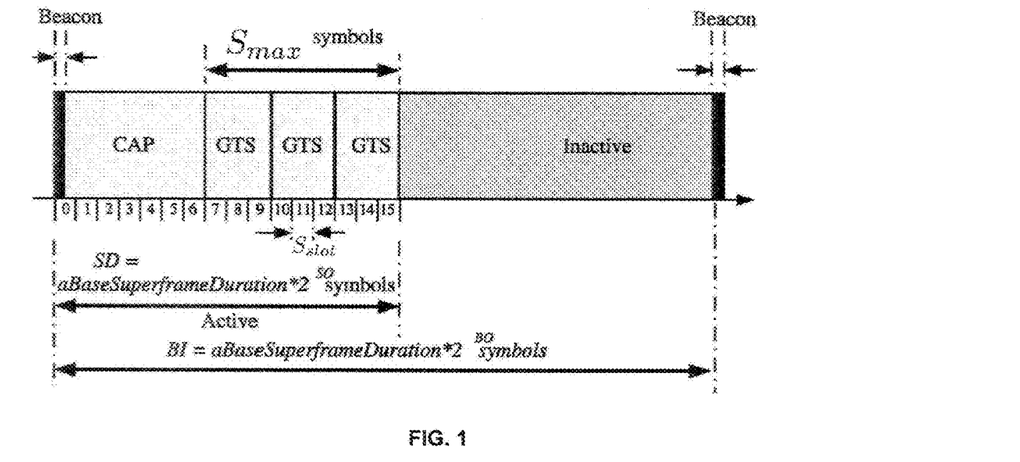
FIG. 1 is a block diagram depicting the superframe structure of the IEEE 802.15.4 standard.

As shown in FIG. 1, time can be divided into superframes. A superframe can be divided into active and inactive periods to maintain the low duty cycle. The active period can be divided into 16 equal slots. The active period can consist of two parts: a contention access period ("CAP") and a contention free period ("CFP"). During CAP, the wireless devices can use a slotted CSMA/CA protocol. All the control commands and request commands can be transmitted during CAP. CFP can be used if a device is assigned with a dedicated GTS. The coordinator can allocate a maximum of seven GTSs to the devices. The CFP starts immediately after CAP and finishes at the end of the active period. During CFP, transmissions can be performed without using CSMA. GTS can be allocated for either uplink or downlink transmission. The coordinator can maintain the beacon interval ("BI"), the slot length, the active period ("SD"), and the inactive period in the beacon order ("BO") and superframe order ("SO") as shown in FIG. 1.

Whenever a device requires a certain guaranteed bandwidth for transmission, the device can send a GTS request command using CSMA/CA during CAP. Upon receiving the request, the coordinator first checks the availability of GTS slots in which the length of CAP must not be shorter than aMinCAPLength. The coordinator informs the device about the allocation of slot in the GTS descriptor in the next beacon frame (FIG. 1). If the device is not included in GTS descriptor for aGTSDesPersistenceTime superframes, then the GTS request is considered to be failed. GTS de-allocation can be performed by the coordinator or by the device itself. For device initiated de-allocation, it sends GTS request with characteristic type subfield set to zero using CSMA/CA during CAP. Similarly, if the coordinator does not receive data from the device in the GTS for at least 2 f superframes, the coordinator will de-allocate the GTS with starting slot subfield set to zero in the GTS descriptor field of the beacon frame for that device where $f=2^{8-BO}$ for $0 \leq BO \leq 8$, and $f=1$ for $9 \leq B \leq 14$.

As pointed out in [6], since the slot length is fixed to a specific duty cycle, GTS slots may be under-utilized due to low data rate transmission and packet with the size smaller than slot length. In addition, regardless of data rate requirement and traffic congestion, the coordinator assigns GTS to the requested devices on the first-come first-serve basis. Therefore, a high data rate device may not receive the GTS allocation.

The problem of GTS allocation was addressed in the literature. A GTS allocation and priority updating scheme was presented in [7] taking latency and fairness of data transmission into account. In [8], i-GAME scheme was proposed to improve the GTS utilization. In this scheme, GTS is shared among multiple devices in a round-robin fashion. This scheme allows more than seven devices to use GTS simultaneously. In [9] an algorithm for GTS allocation during CFP was proposed for the IEEE 802.15.4 standard. This allocation is based on the payload, number of requested slots, and the delay constraint for data transmissions. A method to improve bandwidth utilization of GTS was presented in [10] by dividing the CFP into 16 slots for simultaneous transmissions without any change in GTS descriptor format. In [6] the GTS characteristic field was restructured to accommodate the information about payload demand, delay constraint, and number of periods which can be used to improve bandwidth utilization. However, a device can have only limited choices of payload demand, delay and number of periods due to limited number of bits available in the GTS characteristic field.

GTS allocation schemes were proposed in [8] and [9] considering the delay-guaranteed service. In these schemes, the information of delay requirements needs to be exchanged with the controller which incurs signalling overhead. The scheme in [9] also has high computational complexity due to the execution of a number of algorithms. The scheme in [8]

requires each requesting node to identify flow specification which incurs additional control overhead.

It is, therefore, desirable to provide a method and system for allocating guaranteed time slots for time-critical or delay-sensitive data transmission in IEEE 802.15.4 wireless personal area networks to improve the reliability and bandwidth utilization in these networks.

SUMMARY

A wireless body area sensor network is an emerging technology that can be used in medical, entertainment, and fitness applications. In such a network, several wearable or implanted sensor devices (for example, electrocardiogram ("ECG") sensors, blood pressure sensors, temperature sensors, respiratory sensors, pulse oximeters and accelerometers, to name but a few) can be deployed in or on a person's body to monitor the physiological data of the person. In one embodiment, a body controller unit ("BCU") can collect data from the sensor devices and send the data to a medical center, or other location where a health care professional can monitor the person's physiological data. The IEEE 802.15.1 and the IEEE 802.15.4-based technologies can be suitable for these types of wireless body area sensor networks. The IEEE 802.15.4 standard can support contention-based access mechanisms, as well as guaranteed time slot schemes under a beacon-enabled mode for delay-sensitive data applications.

Under this standard, a GTS transmission scheme can be provided to avoid data packet drop caused by: a) collisions in a contention-based protocol (e.g., carrier sense multiple access/collision avoidance or "CSMA/CA" protocols); b) limited number of allowable retransmissions; and c) the number of back-offs as specified in the IEEE 802.15.4 standard. In a medical sensor network, a GTS allocation scheme can also reduce the energy consumption of the sensor nodes due to carrier sensing.

In some embodiments, an optimization-based scheme is provided to allocate GTS slots to wireless devices. In other embodiments, one GTS request can support the demand of up to $2^5=32$ packets from a device without changing its standard format.

It is an object of the method and system provided herein to design a GTS allocation scheme to cope up with the high loss due to high contention in a bursty traffic load scenario.

It is another object of the method and system provided herein to efficiently utilize guaranteed time slots in the IEEE 802.15.4 standard by providing an optimal GTS allocation scheme that can have potential application for data collection in a wireless body area sensor network.

It is another object of the method and system provided herein to improve the GTS allocation scheme in IEEE 802.15.4-based MAC when used for a large number of medical and physical sensor devices deployed in a WiBaSe-Net. In such an environment, there are uneven traffic generation rates in the different medical sensors, unequal data rate requirements of the sensor devices as well as unequal packet sizes. To efficiently utilize the GTS, an optimization model based on the fractional knapsack problem [5] is formulated and solved to obtain the optimal GTS allocation for the different devices. This optimization model takes the priority which is based on the packet generation rate of each device. Performance evaluation results show that the proposed GTS allocation scheme can improve the utilization of GTS scheme and also improve the performance of data transmission from sensor devices in a WiBaSe-Net when compared to the standard scheme in IEEE 802.15.4.

In one embodiment, the priority and the demand determined from the queue length of the sensor devices can be taken into account to allocate guaranteed time slots to the sensor devices.

In another embodiment, the GTS allocation problem can be formulated as a "fractional knapsack problem" that can be solved to obtain the optimal allocation. As a result, the provided GTS allocation scheme can improve the reliability and bandwidth utilization in the network.

In some embodiments, an optimal GTS allocation scheme is provided with potential application for data collection in a wireless body area sensor network to efficiently utilize the guaranteed time slots in the IEEE 802.15.4 MAC standard. To allocate GTS to the sensor devices, the priority amongst the devices can be determined from the data arrival rates at the devices. In some embodiments, the GTS allocation problem can be formulated as a fractional knapsack problem that can be solved to obtain the optimal allocation. In some embodiments, the GTS allocation scheme can significantly improve packet delivery ratio while decreasing packet drop rate. In some embodiments, the GTS allocation scheme can offer higher packet delivery ratio and, hence, higher bandwidth utilization.

Incorporated by reference into this application in its entirety is a paper written by the within inventors/applicants entitled, "An Optimization-Based GTS Allocation Scheme for IEEE 802.15.4 MAC with Application to Wireless Body-Area Sensor Networks", in the *Proceedings of IEEE International Conference on Communications* (ICC 2010). The paper was published in IEEE Xplore digital library in July 2010.

Broadly stated, in some embodiments, a method is provided for allocating a guaranteed time slot ("GTS") for data or at least one data packet generated from at least one sensor device configured to be disposed on a person for wireless transmission over a wireless body area sensor network, the method comprising the steps of: buffering and storing the data or at least one data packet in a device transmission buffer disposed in the at least one sensor device; determining the amount of data or number of data packets stored in the device transmission buffer; if the amount of data or number of data packets stored in the device transmission buffer of the at least one sensor device is greater than a predetermined data or data packet threshold for the at least one sensor device in a super-frame for wireless transmission over the wireless body area sensor network, the superframe comprising a contention access period ("CAP") and a contention free period ("CFP") further comprising a plurality of guaranteed time slots, then generating a bandwidth demand for the at least one sensor device and transmitting the bandwidth demand to a network coordinator; collecting the bandwidth demands from the at least one sensor device during the CAP; and allocating guaranteed time slots in the CFP for the data or at least one data packet generated by the at least one sensor device.

Broadly stated, in some embodiments, a system is provided for allocating a guaranteed time slot ("GTS") for data or at least one data packet generated from at least one sensor device configured to be disposed on a person for wireless transmission over a wireless body area sensor network, the system comprising: means for buffering and storing the data or at least one data packet in a device transmission buffer disposed in the at least one sensor device; means for determining the amount of data or number of data packets stored in the device transmission buffer; means for generating a bandwidth demand for the at least one sensor device and transmitting the bandwidth demand to a network coordinator if the amount of data or number of data packets stored in the device transmission buffer of the at least one sensor device is greater than a predetermined data or data packet threshold for the at least one sensor device in a superframe for wireless transmission over the wireless body area sensor network, the superframe comprising a contention access period ("CAP") and a contention free period ("CFP") further comprising a plurality of guaranteed time slots; means for collecting the bandwidth demands from the at least one sensor device during the CAP; and means for allocating guaranteed time slots in the CFP for the data or at least one data packet generated by the at least one sensor device.

Broadly stated, in some embodiments, a system is provided for transmitting physiological data of a person, comprising: at least one sensor device disposed on the person, the at least one sensor device configured to sense physiological data of the person, the at least one sensor device configured to buffer and store the physiological data in a device transmission buffer disposed therein, the at least one sensor device comprising first wireless transmission means for wirelessly transmitting the buffered and stored physiological data; a network coordinator configured to wirelessly receive the physiological data transmitted from the at least one sensor device, the network coordinator comprising second wireless transmission means for wirelessly transmitting a superframe to global telecommunications network, the superframe comprising a contention access period ("CAP") and a contention free period ("CFP") further comprising a plurality of guaranteed time slots; means for determining the amount of physiological data stored in the device transmission buffer; means for generating a bandwidth demand for the at least one sensor device and transmitting the bandwidth demand to the network coordinator if the amount of physiological data stored in the device transmission buffer of the at least one sensor device is greater than a predetermined physiological data threshold for the at least one sensor device; means for collecting the bandwidth demands from the at least one sensor device during the CAP; means for allocating guaranteed time slots in the CFP for the physiological data stored in the device transmission buffer; and means for inserting the physiological data stored in the device transmission in the guaranteed time slots of the superframe, wherein the physiological data is transmitted to the global telecommunications network.

DETAILED DESCRIPTION OF EMBODIMENTS

IEEE 802.15.4-Based WiBaSe-Net Model

Figure 2:
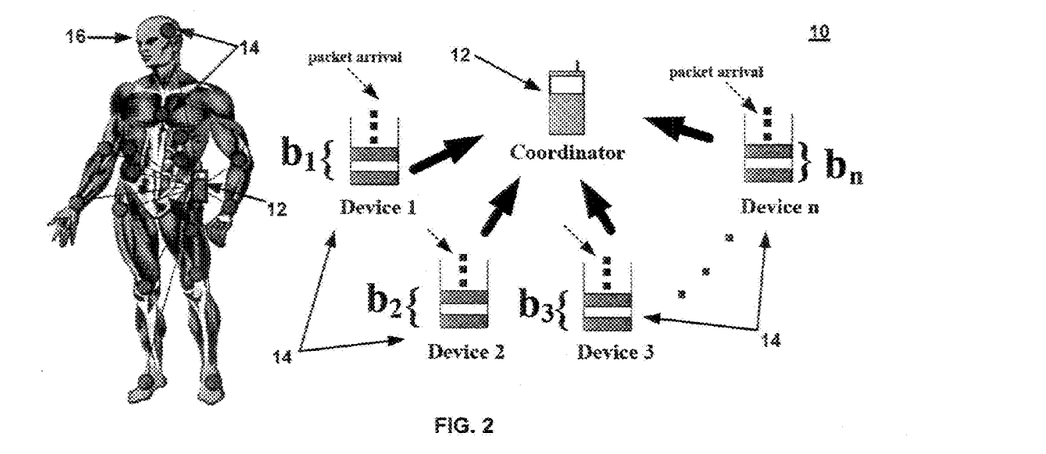
FIG. 2 is a block diagram depicting a WiBASe-Net system model.

In some embodiments, a wireless body area network can be provided based on the IEEE 802.15.4 standard using a star network topology, as shown in FIG. 2 as network 10. In some embodiments, network coordinator (i.e., body controller unit) 12 can collect physiological data from sensor devices 14 deployed in the body of the subject [1]. These sensor devices can comprise electrocardiogram ("ECG") sensors, blood pressure sensors, temperature sensors and accelerometer sensors for a health care monitoring service [11]. In other embodiments, these sensor devices can also comprise blood glucose sensors, blood oxygen sensors, respiratory sensors, pulse oximeter sensors and any other physiological data sensors as well known to those skilled in the art. Data from sensor devices 14 can be collected periodically. However, emergency data can be generated randomly and can be transmitted by the use of dedicated GTS. To support this time-critical data transmission, GTS in the IEEE 802.15.4 standard can be used in some embodiments. In other embodiments, a Bluetooth™ wireless data transmission protocol and hardware, or any other functionally equivalent wireless data transmission protocol and hardware as well known to those skilled in the art, can be used for the transmission of physiological data from sensor devices 14 to network coordinator 12.

In some embodiments, data packets generated in sensor device 14 can be buffered and stored in a device transmission buffer or transmission queue. At the beginning of a superframe, sensor device can check the buffer state, that is, check the number of data packets or amount of data stored in the device transmission buffer. If the number of data packets or amount of data stored in a device transmission buffer is larger than a threshold $T_i$ for the number of data packets from a sensor device i for transmission over the superframe, the device i can generate a bandwidth demand, and the bandwidth demand information can be transmitted to coordinator 12 for GTS slot allocation. During a CAP period, coordinator 12 can collect the bandwidth demands from devices 14. Then, a fractional knapsack problem [5] can be solved by coordinator 12 to allocate GTS to the requesting devices given their priority. The proposed GTS allocation algorithm (as presented herein), which can be based on the solution of the fractional knapsack problem, can be used to optimize the utilization of radio bandwidth in the GTS.

Figure 3:
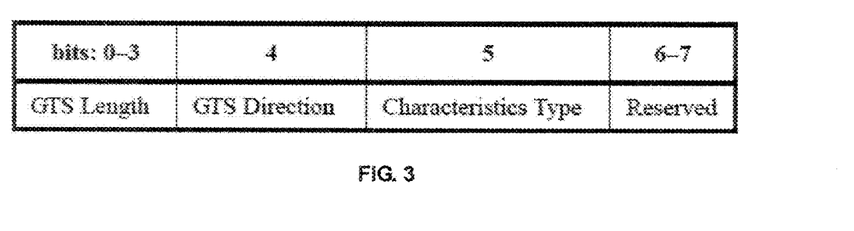
FIG. 3 is a graph depicting the format of the GTS characteristics field in the IEEE 802.15.4 standard.

The bandwidth demand can be considered in terms of the number of packets. In the current standard [3], the size of the characteristic field in the GTS request packet can be one byte (see FIG. 3). In some embodiments, each device 14 can request for the maximum of $D_{max}=32$ packets. The seventh reserved bit can be used to indicate if a particular device 14 needs dedicated a GTS for constant-bit-rate ("CBR") traffic.

In some embodiments, $S_{pkt,i}$ can denote effective packet length in symbols for a given device i. It can be assumed that aMinCAPLength=I symbols and that the length of active period can be SD=($2^{SO}$×aBaseSuperFrameDuration) symbols. The maximum number of symbols that can be transmitted during CFP can be $S_{max}$=(SD−I) symbols. The number of symbols per slot duration can be $S_{slot}$=SD/16 symbols such that $S_{slot} \geq S_{pkt,i}$. For a given device i, $K_i$ can denote the buffer threshold parameter. When the instantaneous queue length in the device is greater than threshold $T_i=K_i S_{slot}/S_{pkt,i}$, device 14 can send a GTS request to coordinator 12. The request can contain the number of packets in the queue immediately after receiving beacon at the beginning of superframe.

If device 14 does not send a GTS request or misses the beacon frame, it can use slotted CSMA/CA to transmit its data. If the request is unsuccessful, device 14 can wait for the next beacon to send another GTS request. Unlike the standard [3], device 14, in order to transmit its data packets, can still compete with other devices during CAP unless a slot is allocated. For each successful transmission, the bandwidth demand can be updated accordingly by coordinator 12 and device 14 itself. In some embodiments, there can be a limit on the transmission delay for a packet in a particular sensor device 14. If the packet exceeds this delay limit, sensor device 14 can simply discard the packet. Coordinator 12 can collect all the GTS requests during CAP and solves the fractional knapsack problem for GTS allocation before transmitting the beacon frame. In so doing, it can save the remaining bandwidth that is not allocated for GTS to use in the next superframe.

Knapsack Problem Formulation

In some embodiments, the set of demands collected and the set of remaining bandwidths to be served for n devices from previous $(t-1)^{th}$ superframe can be denoted by $b=\{b_1^{t-1}, b_2^{t-1}, \ldots, b_n^{t-1}\}$, $b_i^{t-1} \leq D_{max}$, and $r=\{r_1^{t-1}, r_2^{t-1}, \ldots, r_n^{t-1}\}$, respectively. $p=\{p_1, p_2, \ldots, p_n\}$ can denote the corresponding priority. In some embodiments, it can be assumed that coordinator 12 has the information on priority and $S_{pkt,i}$.

For example, this information can be delivered to coordinator 12 at the time of neighbour discovery or association phase. $x_i$ can denote the decision variable of the fractional knapsack problem. This $x_i$ is the fraction of bandwidth that can be used by devices 14 in the upcoming CFP. The fractional knapsack problem can be formulated as follows:

$$\text{Maximize: } \sum_{i=1}^{n} p_i x_i \quad (1)$$

$$\text{Subject to: } \sum_{i=1}^{n} (b_i^{t-1} + r_i^{t-1}) x_i S_{pkt,i} \leq S_{max} \quad (2)$$

$$0 \leq x_i \leq 1 \quad (3)$$

Let $x_i^*$ be the solution of the optimization problem defined in (1)-(3). By solving the fractional knapsack problem, we obtain the bandwidths from the most valuable devices 14 per unit bandwidth demand to fit optimally in the available bandwidth of the CFP. Since the decision variable $x_i^*$ takes any value between zero and one, the fractional knapsack problem can be solved optimally by a greedy algorithm [5] as given in Algorithm 1 (as set out below). The computational complexity of the fractional knapsack algorithm is O(nlog n) [12]. For the purposes of this specification, and the claims herein, the Fractional Knapsack Algorithm is defined as set forth and described below.

Algorithm 1 Fractional Knapsack Algorithm

1: Input: p, m ← (b + r).$S_{pkt}$ and Γ ← $S_{max}$
2: Output: x*
3: sort devices d = {$d_1,d_2,...,d_n$} such that $p_i/m_i \geq p_{i+1}/m_{i+1}$ ∀ device $d_i$ ∈ d
4: foreach device $d_i$ ∈ d do $x_i$ ← 0 end for
5: i ← 1
6: while Γ > 1 do
7:   if $m_i <$ Γ then
8:     $x_i$ ← 1
9:     Γ ← Γ − $m_i$
10:  else
11:    $x_i$ ← Γ/$m_i$
12:    Γ ← 0
13:  end if
14:  i ← i + 1
15: end while Slot Allocation Algorithm In some embodiments, an algorithm can be adopted by the IEEE 802.15.4 standard without any modification to the specification of this standard. In other embodiments, a condition can be imposed to send request on the device side and to use knapsack solution to schedule requested devices for GTS on the coordinator side. For the purposes of this specification, and the claims herein, the Slot Allocation Algorithm is defined by the steps as set forth and described below.

Based on the optimal solution $x_i^*$ obtained from Algorithm 1 at the beginning of $t^{th}$ superframe, the total bandwidth that will be allocated to device i in upcoming slots can be $b_{new,i}^t = (b_i^{t-1}+r_i^{t-1})x_i^*$. The remaining bandwidth is $r_{new,i}^t = (b_i^{t-1}+r_i^{t-1})(1-x_i^*)$. Then, coordinator 12 can convert the allocated number of packets to number of slots such that the GTS idle period can be less than 50%. Let $S_i^t$ be the number of slots allocated to serve $b_{new,i}^t$. The number of packets per slot can be $P_{slot,i}=S_{slot}/S_{pkt,i}$. The number of allocated GTS slots for device i=1, 2, . . . , 7 can be obtained from:

$$S_i^t = \min\left(\left\lfloor \frac{b_{new,i}^t}{P_{slot,i}} \right\rfloor + \Delta S_i, \left\lfloor \frac{S_{max}}{S_{slot}} \right\rfloor - \sum_{i=0}^{i-1} S_j^t \right) \quad (4)$$

Where $S_j^t = 0$ for $j = 0$ and $j > 7$, $\Delta S_i = 1$ if $\text{mod}(b_{new,i}^t, P_{slot,i}) > \frac{1}{2}P_{slot,i}$ and $\Delta S_i = 0$ otherwise.

The fraction of GTS idle due to excessive slot allocation can be given by:

$$GTS_{idle} \leq \frac{\Delta S_i}{2 S_i^t} \quad (5)$$

The final remaining bandwidth to be served can be obtained as follows:

$$r_i^t = \max(0, r_{new,i}^t + b_{new,i}^t - S_i^t P_{slot,i}) \quad (6)$$

$$r_i^t = 0 \text{ for } r_i^t \leq \frac{1}{2}P_{slot,i} \quad (7)$$

The amount of bandwidth that will be served in upcoming slots can be $S_i^t P_{slot,i}$. Coordinator 12 can place the starting slot and slot length $S_i^t$ in the descriptor for each device i. Then, coordinator 12 can update the CAP length and transmits in the beacon frame.

In some embodiments, each device I can maintain the following parameters at the beginning of the $t^{th}$ superframe. $R_i^{t-1}$ can be the number of requested packets in previous superframe, $B_i^t$ can be the current buffer size (number of packets), $S_i^t$ can be the number of slots allocated in current beacon frame, $P_{slot,i}$ can be slot size in terms of number of packets, and $T_i$ can be the buffer threshold. In other embodiments, each device 14 can receive beacon at the beginning of the current superframe. Then, it can update the number of requested packets as follows:

$$R_i^t \leftarrow \max(0, R_i^{t-1} - S_i^t P_{slot,i}) \quad (8)$$

The expression in (8) is equivalent to that in (6). Equation (7) also applies for $R_i^t$. The condition for each device i to send a GTS request can be $B_i^t - R_i^t S_i^t P_{slot,i} > T_i$. If device i satisfies the condition, then it can determine the bandwidth demand from:

$$b_i^t = \min(D_{max\square}, B_i^t - R_i^t - S_i^t P_{slot,i}) \quad (9)$$

If device i transmits GTS request successfully, then it can update the number of requested packets as: $R_i^t = R_i^t + b_i^t$. Otherwise, it can reset bandwidth demand $b_i^t = 0$. If $S_i^t = 0$, the device can access CAP. In this case, device 14 can reduce the value of $R_i^t$ (when $R_i^t$ is non-zero) by one with each successful packet transmission during CAP whereas coordinator 12 can reduce the value of $b_i^t + r_i^t$ (when $b_i^t + r_i^t$ is non-zero) by one. In case device 14 misses a beacon, it also misses GTS and has to reset the value of $R_i^t$. However, device 14 can obtain GTS information in the next received beacon.

Since the buffer threshold $T_i$ can determine the minimum bandwidth to be served per GTS request message, the value of $T_i$ depends on the GTS request rate requirement of the devices. The ideal GTS request rate is $R_{eq,i} = \lambda_i / T_i$, where $\lambda_i$ is the packet generation rate for device i. Since the maximum request rate is one per beacon interval (BI), the minimum buffer threshold can be $T_{min,i} = \lambda_i BI$. As $T_i \leftarrow \infty$ and $R_{eq,i} \leftarrow 0$, the scheme switches to slotted CSMA/CA scheme. To control the number of GTS requests, the buffer threshold can be determined from:

$$T_i \geq \max\left\{ \frac{\sum_{j=1}^{q} N_j \lambda_j}{\sum_{j=1}^{q} N_j}, \max(T_{min,i}, P_{slot,i}) \right\} \quad (10)$$

where $N_j$ is the number of devices with packet rate $\lambda_j$ in the network having devices with q different packet rates.

As an example, consider $P_{slot,i} = 2$, $T_i = 4$ for device i=1,2. At the beginning of $t^{th}$ superframe, let $B_1^t = 5$, $R_1^{t-1} = 0$, $S_1^t = 0$, $B_2^t = 7$, $R_2^{t-1} = 0$, $S_2^t = 0$. From the request condition, the demands can be given by: $b_1^t = 5$, $b_2^t = 7$. Suppose the GTS request is successful for both devices. Then, $R_1^t = 5$, $R_2^t = 7$. Assume that none of these devices could transmit data packets during CAP. Then, at the start of $(t+1)^{th}$ frame, coordinator 12 can allocate slots $S_1^{t+1} = 2$, $S_2^{t+1} = 3$. Assuming $r_1^t = 0$, $r_2^t = 0$, the remaining bandwidths are $r_1^{t+1} = 1$, $r_2^{t+1} = 1$. If both devices receive beacon at $(t+1)^{th}$ frame, then $R_1^{t+1} = 1$, $R_2^{t+1} = 1$. Using (7), $r_1^{t+1} = 0$, $R_1^{t+1} = 0$, $r_2^{t+1} = 0$, $R_2^{t+1} = 0$. If there is no packet arrival at this frame, then $B_1^{t+1} = 5$, $B_2^{t+1} = 7$. Since none of the devices satisfies the GTS request condition, $b_1^{t+1} = 0$, $b_2^{t+1} = 0$. They transmit packets in the allocated slots. If no new packet arrives in the buffer, at the beginning of $(t+2)^{th}$ frame, $B_1^{t+2} = 1$, $B_2^{t+2} = 1$. Since the devices will not be allocated any slots at this frame, $R_1^{t+2} = 0$, $R_2^{t+2} = 0$. However, each of the devices can transmit the remaining packet using CAP competing with other devices. Here, device 1 can transmit 4 packets securely at the cost of 1 GTS request, and thereby, it can save the energy for carrier sensing for transmission of 3 packets while improving GTS utilization.

Simulation and Performance Evaluation
Simulation Setup

To evaluate the performance, the slot allocation algorithm can be implemented on a WPAN model of the NS2 version 2.33. A star topology with single WPAN coordinator and N devices N ∈[10,20] deployed in the area of 1000 mm×1000 mm is considered. Path loss model for body surface analyzed in [13] and [14] is used. The path loss G(f,d) in dB for body surface to body surface propagation at distance d and frequency f=2.4 GHz can be obtained from:

$$G(f,d) = -27.6 \log(d[mm]) - 46.5 \log(f[MHz]) + 157 + W \quad (11)$$

where W is the shadowing component following log normal distribution with standard deviation of 4.4 dB. As in the standard [3], typical values for transmit power of 0 dBm and receiver sensitivity of −85 dBm are used.

Bursty traffic and constant-bit-rate ("CBR") traffic are two common traffic models for medical applications [15]. For CBR traffic (e.g., in ECG streaming), a dedicated GTS slot is required for sustained data transmission. The bandwidth utilization can be improved only if the requested flow rate is close to the slot capacity. However, for bursty traffic (e.g., in respiratory sensor and accelerometer), a dedicated slot may result in bandwidth under-utilization and latency problems if the GTS allocation scheme is not properly designed. For the simulation period of 500 s, each device can generate a demand of $\tau \times \lambda_i$ packets during a time interval $\tau$, where the time interval is assumed to be exponentially distributed with mean value of $\bar{\tau} = 2$ s. The payload size of a packet can be assumed to be 70 bytes for all devices. The data rate can depend on the sensor type, its application and resolution [15]. Six average data rates {12, 9, 7.5, 6, 4.5 and 2.5} kbps are evenly assigned to devices for performance evaluation purpose.

The values of BO and SO can be set to 3. Here, aMinCAPLength can be assumed to be 2 $S_{slot}$ symbols. The transmission delay limit for a newly generated packet at a sensor device can be set to 4 s. With all signalling (e.g., packet transmission time, propagation delay, and IFS period) and packet headers, a device can transmit $2(=S_{slot}/S_{pkt,i})$ packets within a slot duration. For each device, the threshold parameter can be set to $K_i = 7$ such that $T_i = K_i S_{slot}/S_{pkt,i}$ satisfies (10). The priority of the devices can be distributed over the packet rate requirements as follows:

$$\rho_i = \lambda_i - \lambda_{min} + 1 \text{ for } i = 1, 2, \ldots, n. \quad (12)$$

For comparison purposes, the GTS allocation scheme defined in the standard (i.e., FIFO scheme) can be also implemented. In some embodiments, the de-allocation of GTS can be initiated by the device when its queue length is less than half of threshold for five superframes.

Performance Evaluation

The following performance criteria are considered: packet delivery ratio ("PDR"), packet discard rate, link quality indication ("LQI"), packet drop rate, average delay, percentage of GTS idle period, and average probability of GTS transmission. PDR is the ratio between the number of packets successfully received by coordinator 12 and the total packets generated by devices 14 during the simulation period. Packet discard rate indicates the ratio of packet drops due to packet delay limit (i.e., before transmission) to the total packets generated by application. The LQI measurement [3] indicates the quality of received packets in terms of signal to noise ratio ("SNR"). This metric is also useful for channel selection and routing in higher layer. The LQI packet drop rate indicates the ratio of received packet drops to the total transmitted packets.

Figure 4:
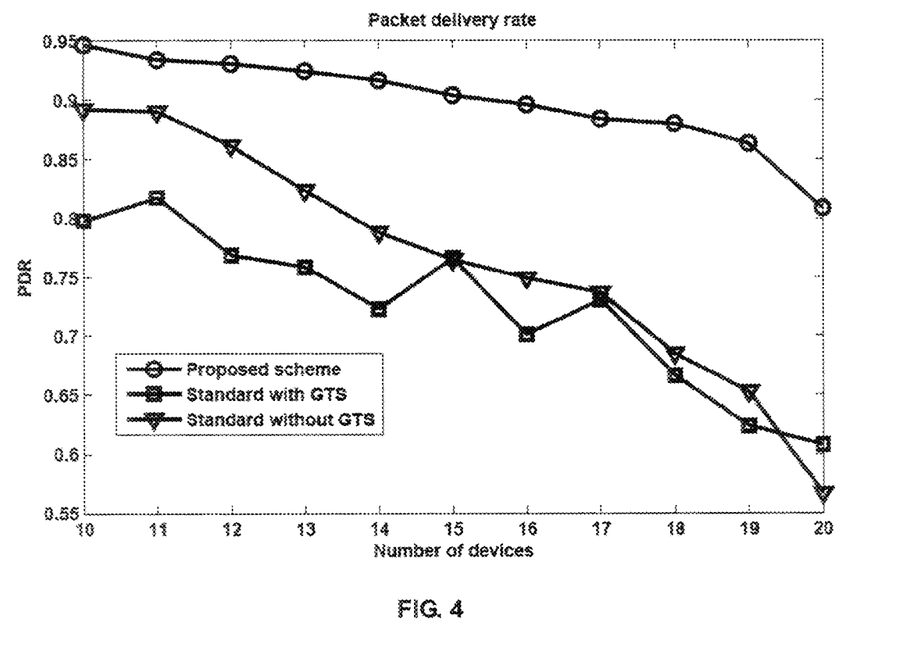
FIG. 4 is an X-Y graph depicting the packet delivery ratio versus number of devices.

FIG. 4 shows the effect of number of devices 14 on PDR. In this figure, the slot allocation algorithm is compared with the beacon-enabled IEEE 802.15.4 MAC with no CFP and standard GTS scheme. The slot allocation algorithm can achieve higher PDR since the algorithm can optimize the utilization of GTS.

Figure 5:
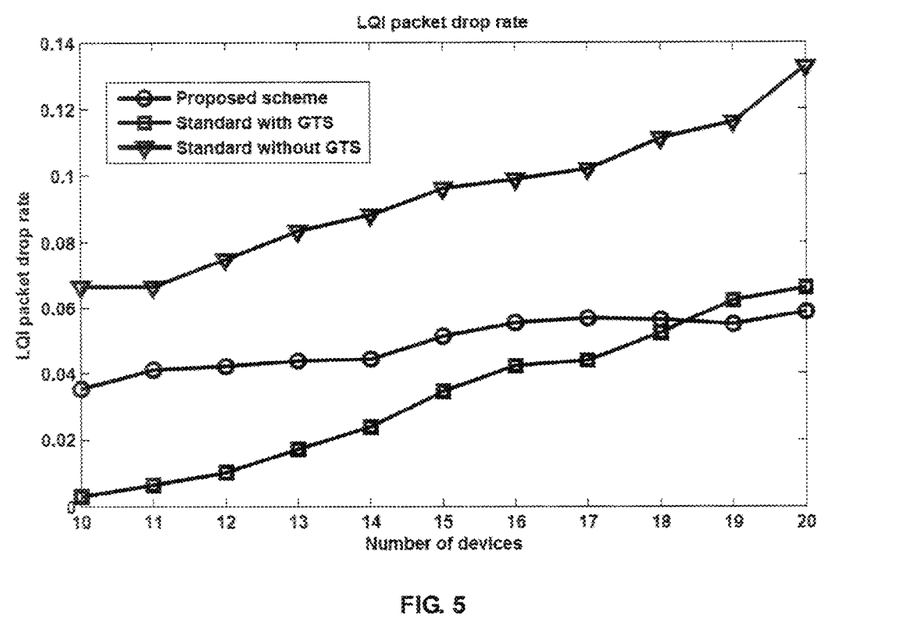
FIG. 5 is an X-Y graph depicting the link quality indication ("LQI") packet drop rate versus number of devices.

An LQI drop occurs when the received SNR is below the threshold (i.e., link quality is too bad due to fading or collision). As the number of devices 14 increases, collision and LQI drop can increase due to high contention during CAP, as shown in FIG. 5. In the standard scheme, dedicated slots and de-allocation procedure reduce the data transmission during CAP. After successful transmission of the request message during CAP, the higher layer protocol is notified of whether the GTS allocation request was successful on the receipt of next beacon frame. In some embodiments, the higher layer protocol can be notified immediately of successful request and, therefore, device 14 can access CAP unless a GTS is allocated. For this reason, devices 14 can have more access to CAP and higher LQI drop rate than that in the standard scheme.

Figure 6:
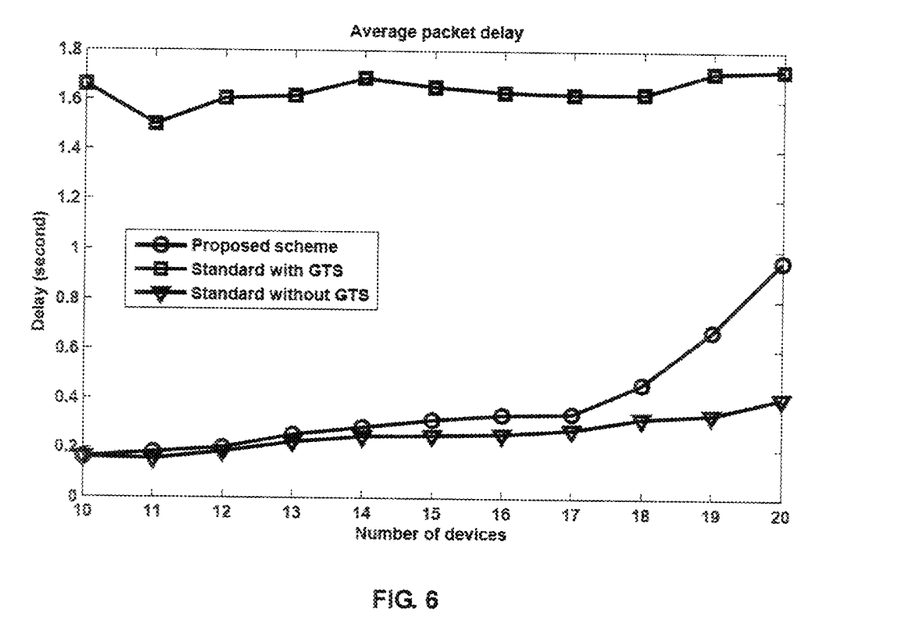
FIG. 6 is an X-Y graph depicting the average packet delay versus number of devices.
Figure 7:
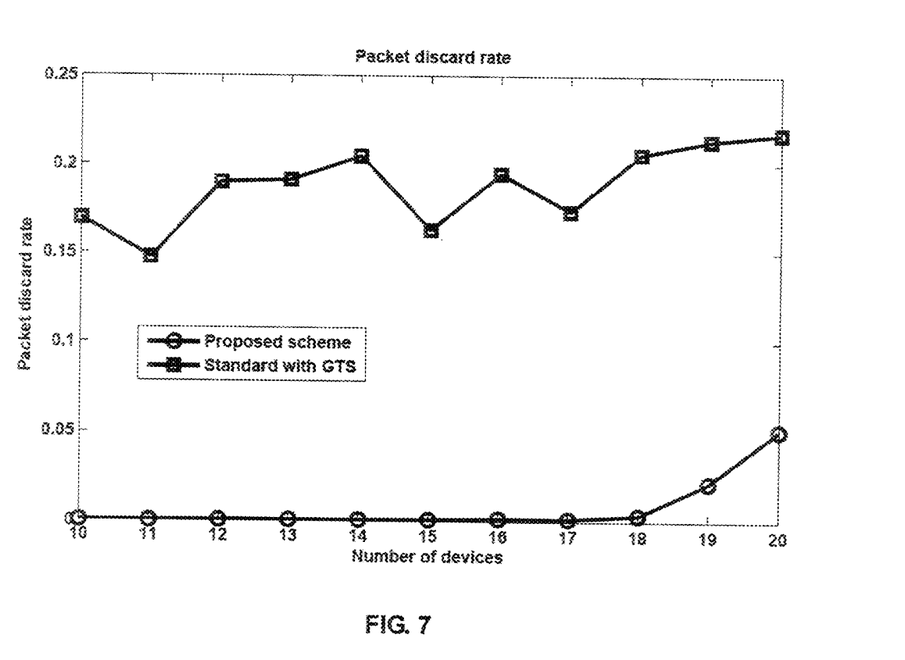
FIG. 7 is an X-Y graph depicting the packet discard rate versus number of devices.

Referring to FIG. 6, the average packet delay is shown. Delay is measured from the time when the packet is first generated by the application at the transmitter to the time when it is successfully received by the application at the receiver. The delay can increase if a device does not receive enough bandwidth during CFP or enough transmission time during CAP. In some embodiments, the packet delay in the proposed scheme can degrade when more than 18 devices request for GTS. Since the sensor devices discard packets for which the transmission delay limit has expired, the packet discard rate can also increase, as shown in FIG. 7. FIGS. 5 and 6 show the trade-off between delay and LQI packet drop.

Figure 8:
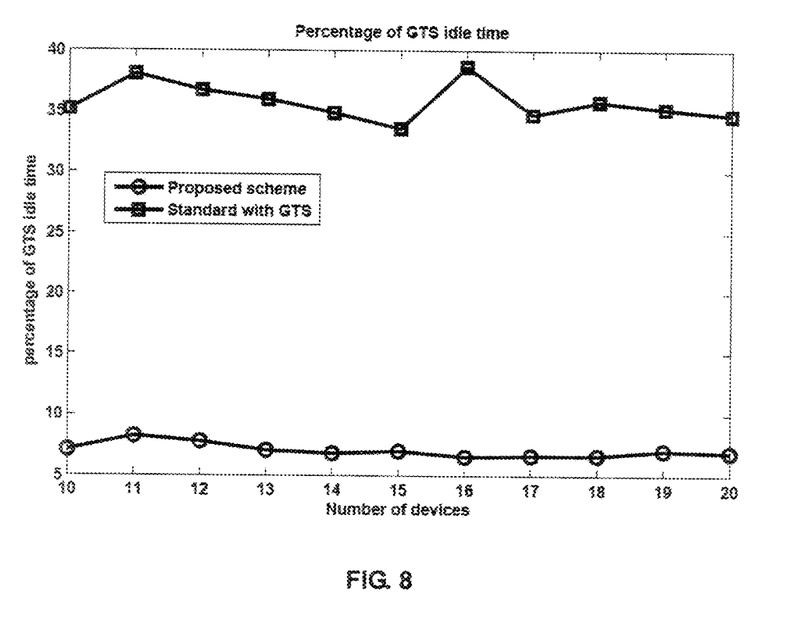
FIG. 8 is an X-Y graph depicting the percentage of guaranteed time slot idle time versus number of devices.

FIG. 8 shows, in some embodiments, the percentage of idle period in the GTS that is not used for data transmission. This idle period can occur due to excessive GTS allocation, or when the devices are unable to receive beacon frames due to poor channel condition, or due to the difference in packet transmission duration and slot duration. In some embodiments, GTS idle period in the proposed scheme described herein can occur only due to the gap in slot duration after transmission of $P_{slot}$ packets and missing of beacons, which can effectively minimize this idle period.

Figure 9:
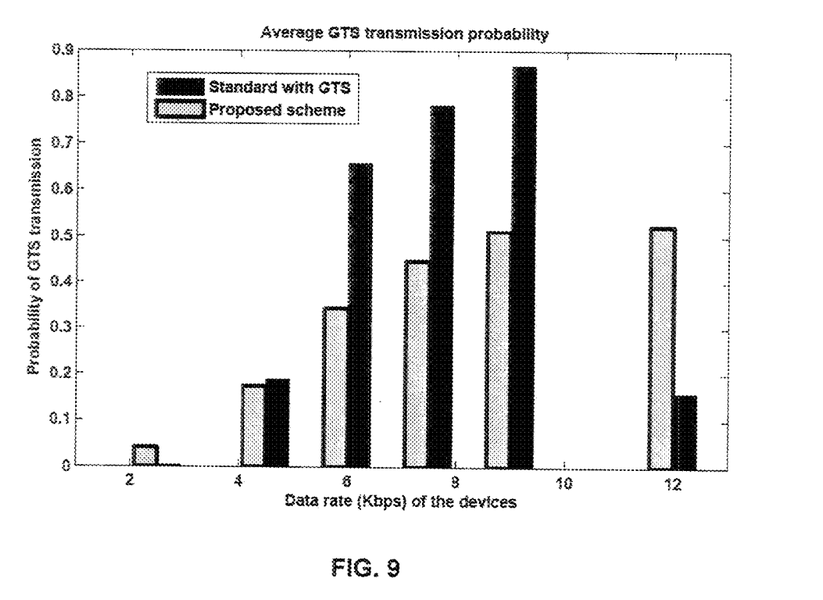
FIG. 9 is a bar graph depicting the probability of guaranteed time slot transmission versus the data rate (in Kb/s) of the devices.

FIG. 9 shows, in some embodiments, the average probability of GTS transmission for the group of devices with different data rates. The probability can be defined as the average ratio of GTS transmissions to total data transmissions for all the devices considered. Again, the allocation of GTS based on the proposed scheme and that in the standard is considered. Since the priority of devices can be proportional to the data rates, the probability of GTS transmission can also be proportionally distributed over different group of devices in the proposed scheme. Using the standard scheme, GTS transmission can be highly unfair for some devices. In contrast, in some embodiments, the proposed scheme described herein is observed to be fair among different devices in respect of GTS allocation.

Figure 10:
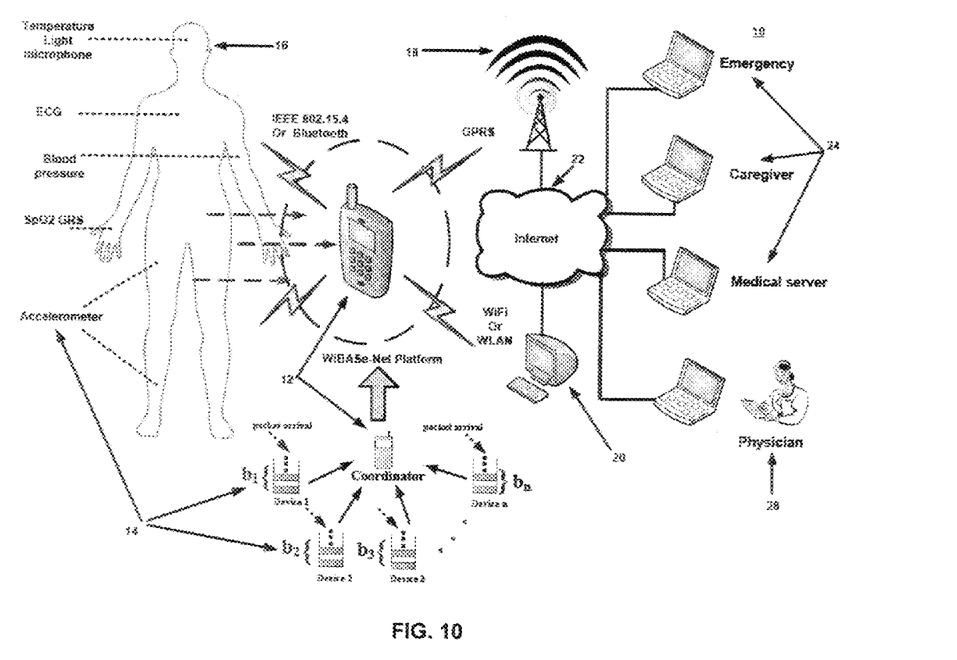
FIG. 10 is a block diagram depicting a system model for a wireless body area sensor network.

Referring to FIG. 10, a wireless body area sensor-networking platform is illustrated that can provide a gateway for a number of sensing devices 14 to external wireless body area sensor network 10. Network coordinator 12, as illustrated in this platform, can collect data from sensors 14. In one embodiment, a media access control ("MAC") protocol, such as IEEE 802.15.4 (i.e., "ZigBee"), can be used as the radio technology platform to provide the wireless data transmission between sensor devices 14 and network coordinator 12 although the BlueTooth® protocol or any other suitable or functionally equivalent wireless transmission protocol can be used, as obvious to those skilled in the art. Using this MAC protocol, sensor devices 14 can buffer the generated packets and request the bandwidth required for the transmission of the packets. In another embodiment, network coordinator 12 can schedule GTS slots to predetermined sensor devices 14 based on the priority of the predetermined sensor devices in relation to the other sensor devices. After collecting information from sensor devices 14, network coordinator 12 can transmit the data to a monitoring centre through an external telecommunications network. In some embodiments, the monitoring centre can comprise one or more terminals or computers 24 operatively connected to internet 22 that can, in turn, be monitored by health care providers 26. In some embodiments, the telecommunications network can comprise computer terminal 20 operatively connected to internet 22, as well known to those skilled in the art, wherein terminal 20 can wirelessly communicate with network coordinator 12 via a IEEE 802.11 wireless local area network connection (i.e., a "Wi-Fi" connection) or via any other functionally equivalent wireless local area network ("WLAN") as well known to those skilled in the art. In other embodiments, the telecommunications network can comprise a general packet radio service ("GPRS") system having GPRS transceiver 18 operatively connected to internet 22, wherein network coordinator 12 can wirelessly communicate with GPRS transceiver 18.

In one embodiment, wireless body area sensor network 10 can be based on the IEEE 802.15.4 standard and can further comprise a star network topology. In this embodiment, network coordinator 12 can comprise a body controller unit that can collect data from the different sensor devices 14 deployed in or on the body of person 16. These sensor devices 14 can generate data packets periodically. The generated packets can then be buffered in a queue for wireless transmission from sensor devices 14 to network coordinator 12.

At the beginning of a superframe for wireless transmission as defined by the IEEE 802.15.4 standard, a sensor device 14 can check the buffer state of the queue. If the number of packets is larger than a predetermined threshold "$T_i$", sensor device "i" can generate a bandwidth demand or request and transmit it to network coordinator 12 by carrying out the steps in a bandwidth demand algorithm (as discussed in more detail below).

With this bandwidth demand information, network coordinator 12 can solve a fractional knapsack problem to allocate guaranteed time slots to the requesting sensor devices. This can be done by first carrying out the steps of a fractional knapsack algorithm to solve the fractional knapsack problem (as discussed in more detail below), and then carrying out the steps of a slot allocation algorithm to assign guaranteed time slots for the data packets generated by the sensor devices (the slot allocation algorithm 3 as discussed in more detail below).

During the contention access period ("CAP") of the superframe, network coordinator 12 can collect the bandwidth demands from sensor devices 14. In one embodiment, "b" can be assumed as a set of bandwidths collected from "n" devices; "p" can be a set of priority values of the devices; and "r" can be a set of remaining bandwidths to be served for sensor devices 14. The operation of sensor devices 14 and network coordinator 12 are shown in the flowchart in the FIG. 11 and FIG. 12 respectively. Table 1, as set below, sets out the parameters for each sensor device "i". For the purposes of this specification, and the claims herein, the Bandwidth Demand Algorithm is defined as set forth and described below, after Table 1.

TABLE 1

| | Parameters for device "i" |
|---|---|
| $D_{max}$ | Demand capacity in terms of number of packets |
| $S_{pkt, i}$ | Effective packet length in number of symbols |
| $S_{slot, i}$ | Number of symbols per slot |
| $P_{slot, i}$ | Number of packets per slot |
| $S_{max}$ | CFP capacity in terms of number of symbols |
| $K_i$ | Buffer threshold parameter |
| $T_i$ | Buffer threshold in terms of number of packets |
| $b_i$ | Bandwidth demand |
| $r_i$ | Remaining bandwidth |
| $p_i$ | Priority value |
| $x_i$ | Knapsack decision variable |
| $S_i$ | Number of slots allocated |
| $R_i$ | Number of requested packets |
| $R_{eqi}$ | GTS request rate |
| $B_i$ | Current buffer length in terms of number of packets |
| $\lambda_i$ | Packet generation rate |

Bandwidth Demand Algorithm—Bandwidth Demand for Each Device "i"

```
1: Input: R_i^{t-1}, P_slot,i, T_i
2: Output: b_i^t
3: foreach beacon received at t^th superframe do
4:     compute B_i^t, S_i^t
5:     update R_i^t ← max(0, R_i^{t-1} - S_i^t P_slot,i)
6:     if B_i^t - R_i^t - S_i^t P_slot,i > T_i then
7:         b_i^t ← min(D_max, B_i^t - R_i^t - S_i^t P_slot,i)
8:         send GTS request with demand b_i^t
9:     end if
10:    if GTS request is successful then
11:        update R_i^t ← R_i^t + b_i^t
12:    else
13:        b_i^t ← 0
14:    end if
15:    if S_i^t = 0 and CAP transmission is successful then
16:        decrement R_i^t (>0) by one
17:    end if
18:    if device misses beacon frame then
19:        R_i^t ← 0
20:    end if
21: end for
```

In one embodiment, the fractional knapsack problem can be formulated as:

$$\text{Maximize} \sum_{i=1}^{n} p_i x_i$$

$$\text{Subject to:} \sum_{i=1}^{n} [(b)_i^{t-1} + r_i^{t-1}] x_i S_{pkt,i} \leq S_{max}$$

$$0 \leq x_i \leq 1$$

The network coordinator can solve this fractional knapsack problem at the beginning of $t^{th}$ frame to allocate GTS to the requesting devices given their priority as given in Algorithm 2 shown below.

Fractional Knapsack Algorithm

```
1: Input: p, m ← (b + r).S_pkt and Γ ← S_max
2: Output: x*
3: sort devices d = {d_1, d_2,...,d_n} such that p_i/m_i ≥ p_{i+1}/m_{i+1} ∀ device d_i ∈ d
4: foreach device d_i ∈ d do x_i ← 0 end for
5: i ← 1
6: while Γ > 1 do
7:     if m_i < Γ then
8:         x_i ← 1
9:         Γ ← Γ - m_i
10:    else
11:        x_i ← Γ/m_i
12:        Γ ← 0
13:    end if
14:    i ← i + 1
15: end while
```

Then, the output of the Knapsack Algorithm (x*) can be used to allocate optimal GTS slots using the Slot Allocation Algorithm shown below.

Slot Allocation Algorithm

```
1: Input: b^{t-1}, r^{t-1}, p
2: Output: S
3: use fractional knapsack algorithm and get x*
4: at the end of t - 1^{th} superframe, calculate bandwidth to serve at next
   superframe t b_{new,i}^t ← (b_i^{t-1} + r_i^{t-1})x*  and remaining bandwidth
   r_{new,i}^t ← (b_i^{t-1} + r_i^{t-1})(1 - x*) for each device i
5: calculate the number of slots allocated to device i as
6: S_i^t ← min(⌊b_{new,i}^t/P_slot,i⌋ + ΔS_i, ⌊S_max/S_slot⌋ - Σ_{j=0}^{i-1} S_j^t)
7: where S_j^t ← 0 for j = 0 and j > 7, ΔS_i ← 1 if mod(b_{new,i}^t, P_slot,i) >
   1/2 P_slot,i and ΔS_i ← 0
   Otherwise
8: final remaining bandwidth is r_i^t ← max(0, b_{new,i}^t + r_{new,i}^t - S_i^t P_slot,i)
9: r_i^t ← 0 for r_i^t ≤ 1/2 P_slot,i
10: Update CAP length and transmit beacon at the beginning of t^{th} super-
    frame
10: if packet is received from device i in CAP then
11:     decrement b_i^t + r_i^t (>0) by one
12: end if
```

Figure 11:
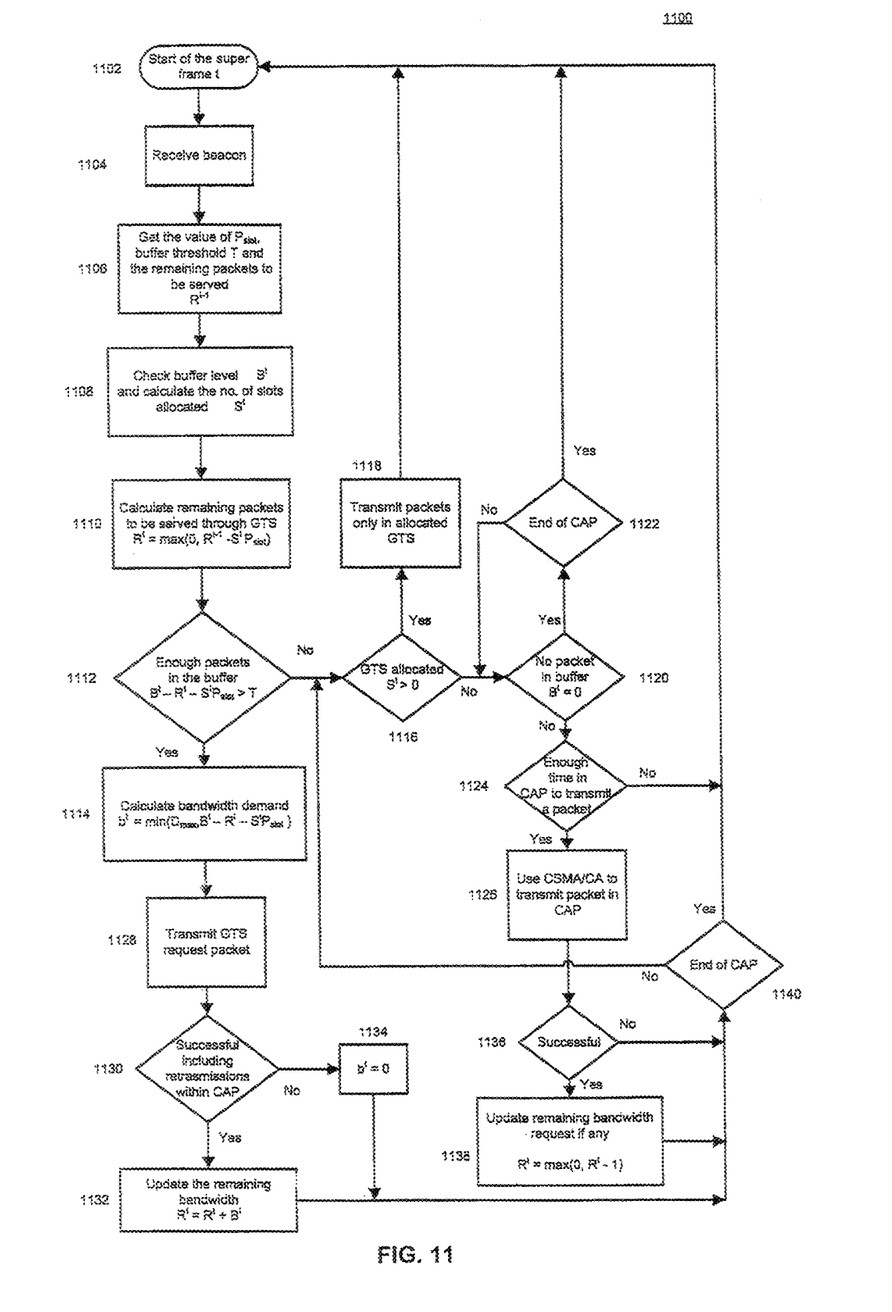
FIG. 11 is a flowchart depicting the operation of a sensor device in a wireless body area sensor network.

Referring to FIG. 11, a flowchart is shown setting out the operation of sensor device 14, in some embodiments, as denoted by process 1100. Process 1100 starts at step 1102 with the start of a superframe t. At step 1104, a beacon can be obtained. At step 1106, the value of $P_{slot}$, buffer threshold T and the remaining packets to be served can be obtained. At step 1108, buffer level $B^t$ can be checked, and the number of slots, $S^t$, to be allocated can be calculated. At step 1110, the remaining number of packets to be served through GTS can be calculated. At step 1112, an inquiry can be made to determine whether there are enough packets in the buffer. If "yes", then the bandwidth demand can be calculated at step 1114. If the answer to the inquiry at step 1112 is "no", then process 1100 can proceed to step 1116.

At step 1128, the GTS packet can be transmitted. At step 1130, an inquiry can be made to determine if the transmission was successful. If "yes", then the remaining bandwidth can be updated at step 1132 wherein process 1100 can then proceed to step 1140. If "no", $b^t$ can be set to "0" at step 1134 wherein process 1100 can then proceed to step 1140. At step 1140, an inquiry can be made to determine if CAP has ended. If "yes", process 1100 can return to step 1102 to repeat. If "no", process 1100 can proceed to step 1116.

At step 1116, an inquiry can be made to determine if the GTS are allocated. If "yes", then only the packets in the allocated GTS can be transmitted at step 1118 following which process 1100 can return to step 1102 to repeat. If "no", process 1100 can proceed to step 1120 where an inquiry can be made to determine whether there is no packet in the buffer (ie, $B^t$=0). If "yes", process 1100 can proceed to step 1122. If "no", process 1100 can proceed to step 1124. At step 1122, an inquiry can be made to determine if CAP has ended. If "yes", process 1100 can return to step 1102 to repeat. If "no", process 1100 can return to step 1120. At step 1124, an inquiry can be made to determine whether there is enough time in CAP to transmit a packet. If "no", process 1100 can return to step 1102 to repeat. If "yes", CSMA/CA can be used to transmit packet in CAP at step 1126 wherein process 1100 can then proceed to step 1136 where an inquiry can be made to determine if the transmission was successful. If "no", process 1100 can proceed to step 1140. If "yes" any remaining bandwidth request can be updated at step 1130 wherein process 1100 can then proceed to step 1140.

Figure 12:
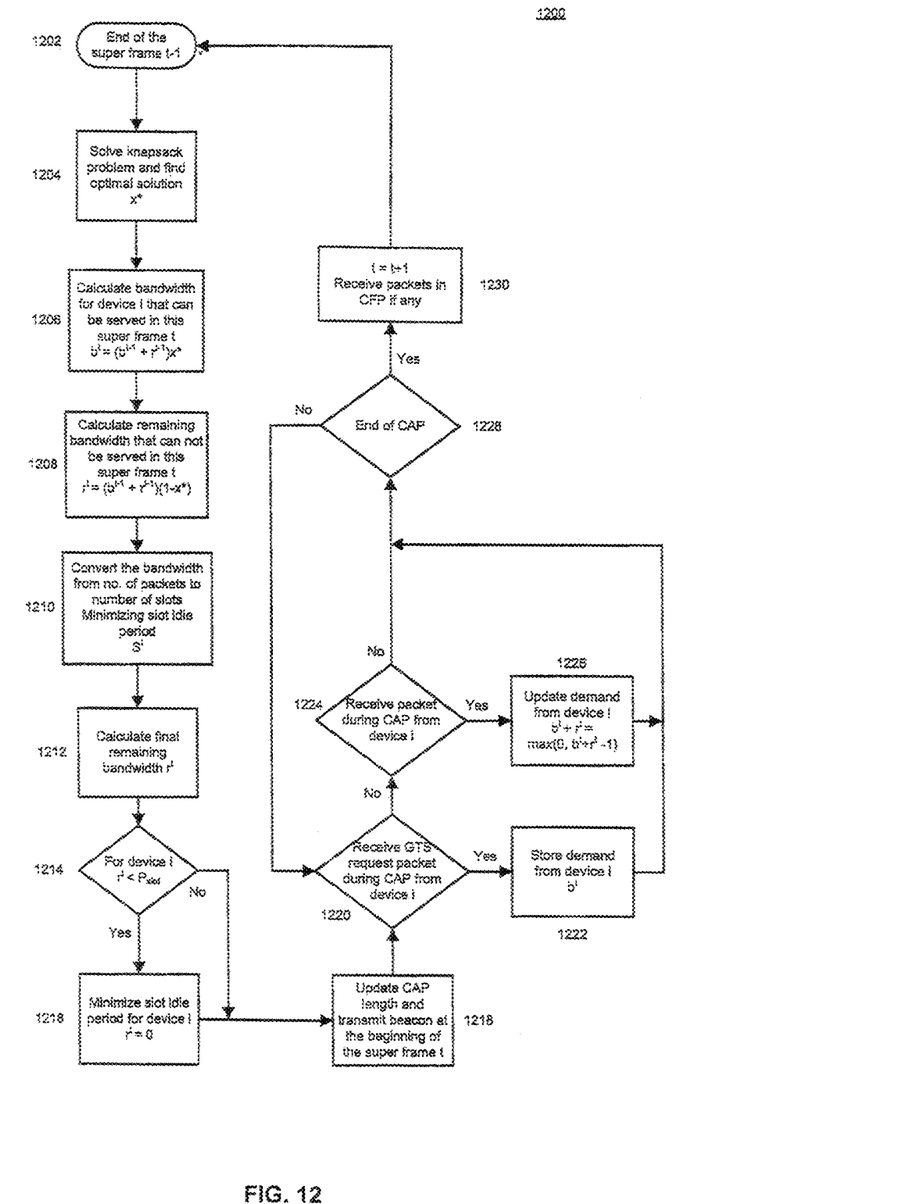
FIG. 12 is a flowchart depicting the operation of a network coordinator in a wireless body area sensor network.

Referring to FIG. 12, a flowchart is shown setting out the operation of network coordinator 12, in some embodiments, as denoted by process 1200. Process 1200 can start at step 1202, which can be the end of superframe t−1, followed by step 1204. At step 1204, the fractional knapsack problem can be solved to find an optimal solution, followed by step 1206. At step 1206, the bandwidth for a device to be served in superframe t can be calculated, followed by step 1208. At step 1208, the remaining bandwidth that cannot be served in superframe t can be calculated, followed by step 1210. At step 1210, the bandwidth can be converted from number of packets to number of slots that can minimize the slot idle period, followed by step 1212. At step 1212, the final remaining bandwidth, $r^t$, can be calculated, followed by step 1214.

At step 1214, an inquiry can be made whether $r^t$ is less than $P_{slot}$. If "yes", the slot idle period for the device can be minimized at step 1216, wherein process 1200 can proceed to step 1218. If "no", process 1200 can proceed to step 1218.

At step 1218, the CAP length can be updated and the beacon transmitted at the beginning of superframe t, wherein process 1200 can proceed to step 1220. At step 1220, an inquiry can be made to determine whether a GTS request packet is received during CAP from the device. If "yes", the demand from the device can be stored at step 1222, wherein process 1200 can proceed to step 1228. If "no"; an inquiry can be made at step 1224 to determine whether a packet is received from the device during CAP. If "no", process 1200 can proceed to step 1228. If "yes", the demand from the device can be updated at step 1226, wherein process 1200 can then proceed to step 1228.

At step 1228, an inquiry can be made to determine whether CAP has ended. If "no", process 1200 can return to step 1220. If "yes", any packets in CFP can be received at step 1230, wherein process 1200 can return to step 1202 to repeat.

Although a few embodiments have been shown and described, it will be appreciated by those skilled in the art that various changes and modifications might be made without departing from the scope of the invention. The terms and expressions used in the preceding specification have been used herein as terms of description and not of limitation, and there is no intention in the use of such terms and expressions of excluding equivalents of the features shown and described or portions thereof, it being recognized that the scope of the invention is defined and limited only by the claims that follow.

REFERENCES

This application incorporates the following documents [1] to [15] by reference in their entirety.

[1] M. A. Hanson, H. C. Powell, A. T. Barth, K. Ringgenberg, B. H. Calhoun, J. H. Aylor, and J. Lach, "Body area sensor networks: Challenges and opportunities," *IEEE Computer*, vol. 42, no. 1, January 2009.

[2] IEEE Standard for Information Technology Part 15.1: Wireless medium access control (MAC) and physical layer (PHY) specifications for wireless personal area networks (WPANs), *IEEE Standard 802.15.4 Working Group Std.*, 2005.

[3] IEEE Standard for Information Technology Part 15.4: Wireless Medium Access Control (MAC) and Physical Layer (PHY) Specifications for Low-Rate Wireless Personal Area Networks (LR-WPANs), *IEEE Standard 802.15.4 Working Group Std.*, 2006.

[4] J. Espina, T. Falck and O. Mlhens, "Network topologies, communication protocols, and standards," *Body Sensor Networks*, Ed. Javier Espina, Springer, London, December 2007.

[5] J. Noga and V. Sarbua, "An online partially fractional fractional knapsack problem," in *Proceedings of International Symposium on Parallel Architectures, Algorithms and Networks (ISPAN'05)*, December 2005.

[6] P. Kumar, M. Gunes, A. Al Mamou, and I. Hussain, "Enhancing IEEE 802.15.4 for low-latency, bandwidth, and energy critical WSN applications," in *Proceedings of 4th International Conference on Emerging Technologies (ICET'08)*.

[7] Y.-K. Huang, A.-C. Pang, and T.-W. Kuo, "An adaptive GTS allocation with low latency and fairness considerations for IEEE 802.15.4," *IEEE Transactions on Parallel and Distributed Systems*, vol. 19, no. 5, May 2008.

[8] A. Koubaa, M. Alves, and E. Tovar, "i-GAME: An implicit GTS allocation mechanism in IEEE 802.15.4 for time-sensitive wireless sensor networks," in *Proceedings of 18th Euromicro Conference on Real-Time Systems*, 2006.

[9] C. Na, Y. Yang, and A. Mishra, "An optimal GTS scheduling algorithm for time-sensitive transactions in IEEE 802.15.4 networks," *Computer Networks*, vol. 52, no. 13, pp. 2543-2557, September 2008.

[10] L. Cheng, A. G. Bourgeois, and X. Zhang, "A new GTS allocation scheme for IEEE 802.15.4 networks with improved bandwidth utilization," in *Proceedings of International Symposium on Communications and Information Technologies (ISCIT'07)*, 2007.

[11] U. Varshney, "Pervasive healthcare and wireless health monitoring," *Mobile Networks and Applications*, vol. 12, no. 2-3, Springer Netherlands, June, 2007.

[12] T. H. Cormen, C. E. Leiserson, R. L. Rivest, and C. Stein, *Introduction to Algorithms*, The MIT press, 2001.

[13] T. Aoyagi, J. Takada, K. Takizawa, N. Katayama, T. Kobayashi, K. Y. Yazdandoost, H. B. Li, and R. Kohno, "Channel models for wearable and implantable WBANs," *IEEE 802.15 Working Group Document, IEEE 802.15-08-0416-02-0006*, July 2008.

[14] J. Takada, T. Aoyagi, K. Takizawa, N. Katayama, H. Sawada, T. Kobayashi, K. Y. Yazdandoost, H. b. Li, and R. Kohno, "Static propagation and channel models in body area," *COST 2100 6th Management Committee Meeting*: TD(08)639, Lille, France, October 2008.

[15] A. Ahmad, A. Riedl, W. J. Naramore, N.Y. Chou, and M. S. Alley, "Scenario-based traffic modeling for data emanating from medical instruments in clinical environment," *2009 WRI World Congress on Computer Science and Information Engineering*, Mar. 31-Apr. 2, 2009.

We claim:

1. A method for allocating a guaranteed time slot ("GTS") for data or at least one data packet generated from at least one sensor device configured to be disposed on a person for wireless transmission over a wireless body area sensor network, the method comprising the steps of:
- a) buffering and storing the data or at least one data packet in a device transmission buffer disposed in the at least one sensor device;
- b) determining the amount of data or number of data packets stored in the device transmission buffer;
- c) when the amount of data or number of data packets stored in the device transmission buffer of the at least one sensor device is greater than a predetermined data or data packet threshold for the at least one sensor device in a superframe for wireless transmission over the wireless body area sensor network, the superframe comprising a contention access period ("CAP") and a contention free period ("CFP") further comprising a plurality of guaranteed time slots, then generating a bandwidth demand for the at least one sensor device and transmitting the bandwidth demand to a network coordinator, wherein the step of generating the bandwidth demand comprises carrying out the steps of a bandwidth demand algorithm comprising the steps of:
  - i. receiving a beacon frame at a beginning of the superframe,
  - ii. computing the amount of data packets in the device transmission buffer of the at least one sensor device ("$B_i^t$"), the number of guaranteed time slots for the at least one sensor device ("$S_i^t$") and a number of requested data packets requested in a previous superframe for the at least one sensor device ("$R_i^{t-1}$"),
  - iii. when the superframe is a first frame, setting a number of requested packets for the at least one sensor device ("$R_i^t$") to zero, otherwise setting $R_i^t$ to $(R_i^{t-1} - S_i^t P_{slot,i})$ where $P_{slot,i}$ is a number of data packets per slot for the at least one sensor device,
  - iv. when $B_i^t - R_i^t - S_i^t P_{slot,i}$ is greater than the data packet threshold, setting a bandwidth demand ("$b_i^t$") to a lesser of $V_i^t - R_i^t - S_i^t P_{slot,i}$ and $D_{max}$, where $D_{max}$ is a demand capacity in terms of packets of the superframe,
  - v. when $b_i^t$ is successfully transmitted, updating $R_i^t$ to be $R_i^t + b_i^t$, otherwise when $b_i^t$ is not successfully transmitted, setting $b_i^t$ to zero, and
  - vi. when $S_i^t$ is equal to zero and when $R_i^t$ is greater than zero, decrementing $R_i^t$ by one for each packet transmitted during the CAP;
- d) collecting the bandwidth demands from the at least one sensor device during the CAP; and
- e) allocating guaranteed time slots in the CFP for the data or at least one data packet generated by the at least one sensor device.

2. The method as set forth in claim 1 wherein the step of allocating guaranteed time slots comprises the steps of:
- a) carrying out the steps of a fractional knapsack algorithm to prioritize the data or at least one data packet generated by the at least one sensor device; and
- b) carrying out the steps of a slot allocation algorithm to assign guaranteed time slots to the prioritized data or at least one data packet.

3. The method as set forth in claim 1, wherein the wireless body area sensor network comprises a wireless body area sensor network.

4. A system for allocating a guaranteed time slot ("GTS") for data or at least one data packet generated from at least one sensor device configured to be disposed on a person for wireless transmission over a wireless body area sensor network, the system comprising:
- a) means for buffering and storing the data or at least one data packet in a device transmission buffer disposed in the at least one sensor device;
- b) means for determining the amount of data or number of data packets stored in the device transmission buffer;
- c) means for generating a bandwidth demand for the at least one sensor device and transmitting the bandwidth demand to a network coordinator when the amount of data or number of data packets stored in the device transmission buffer of the at least one sensor device is greater than a predetermined data or data packet threshold for the at least one sensor device in a superframe for wireless transmission over the wireless body area sensor network, the superframe comprising a contention access period ("CAP") and a contention free period ("CFP") further comprising a plurality of guaranteed time slots;
- d) means for collecting the bandwidth demands from the at least one sensor device during the CAP, wherein the means for generating the bandwidth demand further comprise means for carrying out the steps of a bandwidth demand algorithm, wherein the bandwidth demand algorithm comprises the steps of:
  - i. receiving a beacon frame at a beginning of the superframe,
  - ii. computing the amount of data packets in the device transmission buffer of the at least one sensor device ("$B_i^t$"), the number of guaranteed time slots for the at least one sensor device ("$S_i^t$") and a number of requested data packets requested in a previous superframe for the at least one sensor device ("$R_i^{t-1}$"),
  - iii. when the superframe is a first frame, setting a number of requested packets for the at least one sensor device ("$R_i^t$") to zero, otherwise setting $R_i^t$ to $(R_i^t - S_i^t P_{slot,i})$ where $P_{slot,i}$ is a number of data packets per slot for the at least one sensor device,
  - iv. when $B_i^t - R_i^t - S_i^t P_{slot,i}$ is greater than the data packet threshold, setting a bandwidth demand ("$b_i^t$") to a lesser of $B_i^t - R_i^t - S_i^t P_{slot,i}$ and $D_{max}$, where $D_{max}$ is a demand capacity in terms of packets of the superframe,
  - v. when $b_i^t$ is successfully transmitted, updating $R_i^t$ to be $R_i^t + b_i^t$, otherwise when $b_i^t$ is not successfully transmitted, setting $b_i^t$ to zero, and
  - vi. when $S_i^t$ is equal to zero and when $R_i^t$ is greater than zero, decrementing $R_i^t$ by one for each packet transmitted during the CAP; and
- e) means for allocating guaranteed time slots in the CFP for the data or at least one data packet generated by the at least one sensor device.

5. The system as set forth in claim 4, wherein the means for allocating guaranteed time slots further comprises:
- a) means for carrying out the steps of a fractional knapsack algorithm to prioritize the data or at least one data packet generated by the at least one sensor device;
- b) means for carrying out the steps of a slot allocation algorithm to assign guaranteed time slots to the prioritized data or at least one data packet.

6. The system as set forth in claim 4, wherein the wireless body area sensor network comprises a wireless body area sensor network.

7. A system for transmitting physiological data of a person, comprising:
- a) at least one sensor device disposed on the person, the at least one sensor device configured to sense physiological data of the person, the at least one sensor device configured to buffer and store the physiological data in a device transmission buffer disposed therein, the at least one sensor device comprising first wireless transmission means for wirelessly transmitting the buffered and stored physiological data;
b) a network coordinator configured to wirelessly receive the physiological data transmitted from the at least one sensor device, the network coordinator comprising second wireless transmission means for wirelessly transmitting a superframe to global telecommunications network, the superframe comprising a contention access period ("CAP") and a contention free period ("CFP") further comprising a plurality of guaranteed time slots;
c) means for determining the amount of physiological data stored in the device transmission buffer;
d) means for generating a bandwidth demand for the at least one sensor device and transmitting the bandwidth demand to the network coordinator when the amount of physiological data stored in the device transmission buffer of the at least one sensor device is greater than a predetermined physiological data threshold for the at least one sensor device, wherein the means for generating the bandwidth demand further comprise means for carrying out the steps of a bandwidth demand algorithm, wherein the bandwidth demand algorithm comprises the steps of:
  i. receiving a beacon frame at a beginning of the superframe,
  ii. computing the amount of data packets in the device transmission buffer of the at least one sensor device ("$B_i^t$"), the number of guaranteed time slots for the at least one sensor device ("$S_i^t$") and a number of requested data packets requested in a previous superframe for the at least one sensor device ("$R_i^{t-1}$"),
  iii. when the superframe is a first frame, setting a number of requested packets for the at least one sensor device ("$R_i^t$") to zero, otherwise setting $R_i^t$ to ($R_i^{t-1} - S_i^t P_{slot,i}$) where $P_{slot,i}$ is a number of data packets per slot for the at least one sensor device,
  iv. when $B_i^t - R_i^t - S_i^t P_{slot,i}$ is greater than the data packet threshold, setting a bandwidth demand ("$b_i^t$") to a lesser of $B_i^t - R_i^t - S_i^t P_{slot,i}$ and $D_{max}$, where $D_{max}$ is a demand capacity in terms of packets of the superframe,
  v. when $b_i^t$ is successfully transmitted, updating $R_i^t$ to be $R_i^t + b_i^t$, otherwise when $b_i^t$ is not successfully transmitted, setting $b_i^t$ to zero, and
  vi. when $S_i^t$ is equal to zero and when $R_i^t$ is greater than zero, decrementing $R_i^t$ by one for each packet transmitted during the CAP;
e) means for collecting the bandwidth demands from the at least one sensor device during the CAP;
f) means for allocating guaranteed time slots in the CFP for the physiological data stored in the device transmission buffer; and
g) means for inserting the physiological data stored in the device transmission in the guaranteed time slots of the superframe, wherein the physiological data is transmitted to the global telecommunications network.

8. The system as set forth in claim 7, wherein the means for allocating guaranteed time slots further comprises:
a) means for carrying out the steps of a fractional knapsack algorithm to prioritize the data or at least one data packet generated by the at least one sensor device; and
b) means for carrying out the steps of a slot allocation algorithm to assign guaranteed time slots to the prioritized data or at least one data packet.

9. The system as set forth in claim 7, wherein the first wireless transmission means is configured to operate in a wireless body area sensor network.

10. The system as set forth in claim 7, wherein the second wireless transmission means is configured to operate in a wireless local area network.

11. The system as set forth in claim 7, further comprising a monitoring centre operatively connected to the global telecommunications network and configured to receive the physiological data transmitted by the network coordinator wherein the physiological data can be monitored by a health care provider.

* * * * *

UNITED STATES PATENT AND TRADEMARK OFFICE
CERTIFICATE OF CORRECTION

PATENT NO. : 8,976,763 B2  Page 1 of 1
APPLICATION NO. : 12/974718
DATED : March 10, 2015
INVENTOR(S) : Bharat Shrestha et al.

It is certified that error appears in the above-identified patent and that said Letters Patent is hereby corrected as shown below:

On the title page item (73), "ALberta" should read --Alberta--;

In the Specification,

Column 8, line 24, change "$r^t_{new}$" to --$r^t_{new,i}$--; and

In the Claims,

Column 17, line 39, change "$V^t_i$" to --$B^t_i$--.

Signed and Sealed this
Eleventh Day of August, 2015

Michelle K. Lee
*Director of the United States Patent and Trademark Office*